US006339223B1

United States Patent
Motomura et al.

(10) Patent No.: US 6,339,223 B1
(45) Date of Patent: Jan. 15, 2002

(54) APPARATUS FOR TRUNCATION CORRECTION OF TRANSMISSION CT AND NUCLEAR MEDICAL DIAGNOSTIC APPARATUS USING THE SAME

(75) Inventors: Nobutoku Motomura, Nasu-gun; Takashi Ichihara, Otawara, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/348,665

(22) Filed: Jul. 6, 1999

(30) Foreign Application Priority Data

Jul. 7, 1998 (JP) .............................. 10-191717

(51) Int. Cl.[7] .............................................. A61B 5/00
(52) U.S. Cl. .............................. 250/363.07; 250/363.04
(58) Field of Search ....................... 250/363.07, 363.04, 250/395

(56) References Cited

U.S. PATENT DOCUMENTS

| 5,055,687 | A | | 10/1991 | Ichihara | |
|---|---|---|---|---|---|
| 5,210,421 | A | | 5/1993 | Gullberg et al. | |
| 5,338,936 | A | * | 8/1994 | Gullberg et al. | 250/363.04 |
| 5,532,490 | A | * | 7/1996 | Gullberg et al. | 250/363.04 |
| 5,565,684 | A | * | 10/1996 | Gullberg et al. | 250/363.04 |
| 5,640,436 | A | * | 6/1997 | Kawai et al. | 378/4 |
| 5,705,819 | A | * | 1/1998 | Takahashi et al. | 250/363.04 |
| 5,752,916 | A | * | 5/1998 | Guerard et al. | 250/363.04 |
| 5,814,817 | A | * | 9/1998 | Guillemaud et al. | 250/363.04 |

OTHER PUBLICATIONS

Tin–Su Pan, et al. "Reduction of Truncation Artifacts in Fan Beam Transmission by Using Parallel Beam Emission Data", IEEE Transactions on Nuclear Science, vol. 42, No. 4, Aug. 1995, pp. 1310–1320.

* cited by examiner

Primary Examiner—Constantine Hannaher
Assistant Examiner—Otilia Gabor
(74) Attorney, Agent, or Firm—Oblon, Spivak, McClelland, Maier & Neustadt, P.C.

(57) ABSTRACT

SPECT data is collected to produce a SPECT image and transmission CT projection data is collected to produce a transmission CT image. The contours of the body of a subject under examination is extracted from the SPECT image. Using data representing the contours of the body, a portion of the transmission CT projection data is approximated by a curve. The sum of the curve-approximated transmission CT projection data and the center of gravity of the transmission CT image are computed. The truncated portion is estimated from the sum of the transmission CT projection data and the center of gravity of the transmission CT image and the transmission CT projection data is then corrected.

The correction of the transmission CT projection data involves producing (extrapolation) anew a curve represented by a quadratic polynomial for that region (truncated region) of the transmission CT projection data which has been approximated tentatively by an ellipse in order to determine the sum and the center of gravity.

23 Claims, 3 Drawing Sheets

APPARATUS FOR TRUNCATION CORRECTION OF TRANSMISSION CT AND NUCLEAR MEDICAL DIAGNOSTIC APPARATUS USING THE SAME

BACKGROUND OF THE INVENTION

The present invention relates to the correction of truncation of transmission computerized tomography (TCT) data.

A single photon emission CT (SPECT) apparatus, which is one type of nuclear medical diagnostic apparatus, detects gamma (γ) rays emitted from radioisotope (RI) injected into the human body under examination and measures the RI distribution within the human body. The gamma rays decay within the human body. Thus, qualitative measurement requires measuring how gamma rays decay in areas of the human body through transmission CT using an external gamma ray source and correcting the RI measurements accordingly.

Of TCTs using an external gamma ray source, the TCT using a fan-beam collimator, i.e., the TCT that uses a fan beam not a parallel beam, collimates gamma rays at two places: one near the source and one near the detector. Collimating the gamma rays reduces the effects of scattered rays, obtaining TCT data useful in measuring the distribution of coefficients of decay of gamma rays within the human body.

However, the fan beam-based TCT, while being little affected by scattered rays, has a disadvantage of the effective field of view being small in comparison with the parallel beam-based TCT. In measuring the body of an object under examination, therefore, a part of the body may protrude from the effective field of view.

The reconstruction of projection data without taking into consideration that a part of the body under examination is protruding from the effective field of view would produce artifacts due to imperfect reconstruction resulting from truncation errors.

Thus, high-precision TCT data cannot be obtained, which leads to a failure to take a measurement of the distribution of coefficients of decay of gamma rays with precision in SPECT using TCT data.

A conventional technique related to truncation correction of TCT data is described in "Reduction of Truncation Artifacts in Fan Beam Transmission by Using Parallel Beam Emission Data" by Tin-Su Pan, Michael A. King, et al., IEEE TRANSACTIONS ON NUCLEAR SCIENCE, VOL. 42, NO. 4, AUGUST 1995. This conventional technique extracts the contours of the body and the lung from SPECT data to obtain outline information and uses the outline information in truncation correction of TCT data. However, this technique is not practical. The reason is that the extraction of the contours of the lung from SPECT data is difficult and tentative coefficients of decay of gamma rays have to be used.

BRIEF SUMMARY OF THE INVENTION

It is therefore an object of the present invention to provide an apparatus and method which allow precise TCT data having truncation errors corrected to be obtained.

According to the present invention, there is provided a truncation correction apparatus for transmission CT comprising: first acquiring means for acquiring emission data; second acquiring means for acquiring TCT projection data; calculating means for calculating a center of gravity of a TCT image and a total of the TCT projection data from the emission data and the TCT projection data; and correcting means for correcting the TCT projection data on the basis of the center of gravity of the TCT image and the total of the TCT projection data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
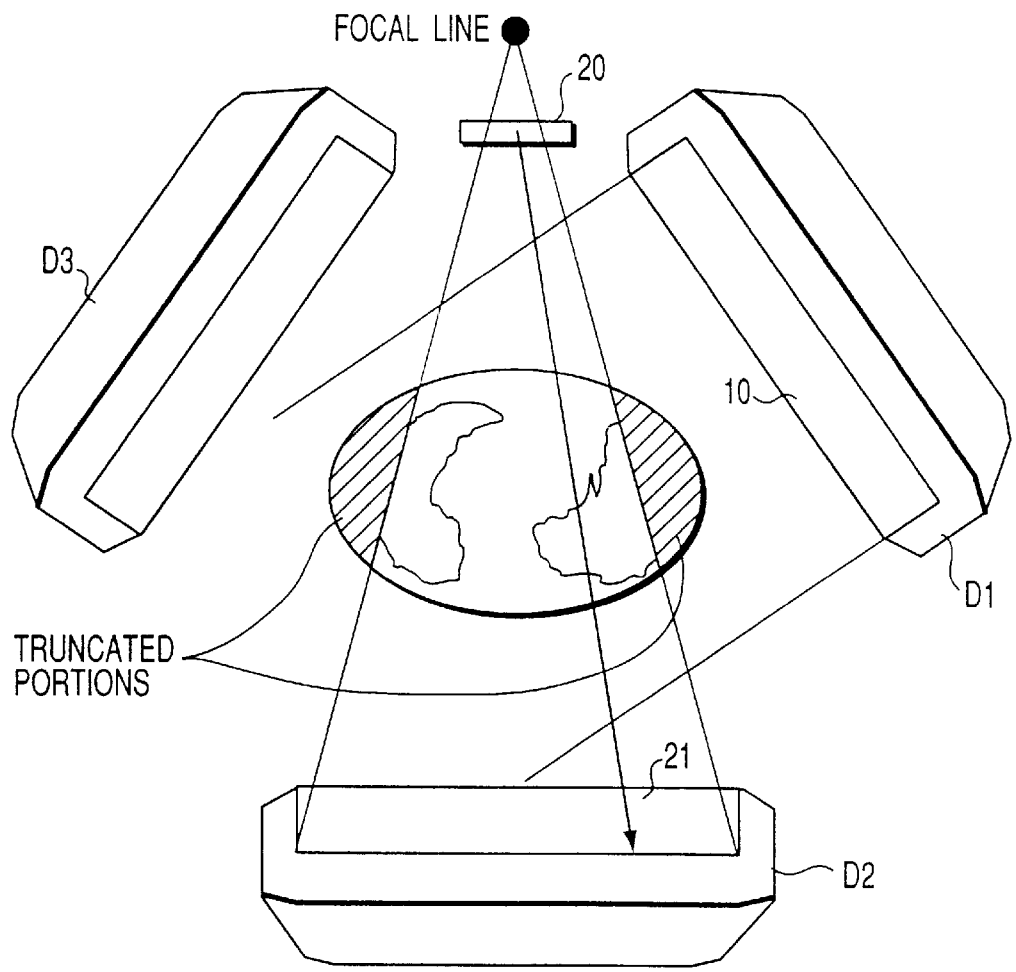
FIG. 1 is a schematic illustration of a TCT/SPECT system according to an embodiment of the present invention.

FIG. 1 shows a schematic configuration of a fan beam-based SPECT/TCT system according to an embodiment of the present invention. This system is configured such that SPECT data and TCT data can be collected at the same time.

The system is equipped with three detectors D1, D2 and D3. The detector D1 used to collect the SPECT data has a parallel hole collimator 10. The detector D2, which is opposed to an external source 20 of gamma rays and is used to collect the TCT data, has a fan beam collimator 21. At least one of the detectors D1, D2 and D3 is equipped with a parallel hole collimator to allow the collection of truncation-free SPECT data.

The detectors and the collimators are rotatably mounted to a frame and arranged to collect SPECT data and TCT data while revolving around a subject under examination in small angular steps. To each of the detectors D1 to D3 is attached a data collection unit which determines the count of incident gamma rays in each position of incidence. Based on the outputs of the detectors D1, D2 and D3, the data collection units determine two-dimensional position information of incidence of gamma rays and energy values of incident gamma ray on the detecting surface and count gamma rays whose energy values fall within a given range in each position of incidence. The data collection units collect the counts of gamma rays in each two-dimensional position of incidence each time the detectors revolve in a step.

The external gamma ray source 20 consists of a relatively small, surface source and is placed so that it is opposed to the fan beam collimator 21 with a human body under examination interposed therebetween. By shaping the external gamma ray source 20 used to collect TCT data into a surface form not a line form, as in this embodiment, the radius of rotation of the detectors is made movable. This allows TCT data to be collected to conform to the size of the human body under examination.

As described previously, since the fan beam TCT system collimates gamma rays in the two places in the proximity of the source and the detector, scattered rays are reduced, allowing the coefficients of decay of gamma rays within the body to be measured precisely. However, since the fan beam collimator is small in the effective field of view, when the body of a subject under examination is to be measured, a part of the body may protrude from the field of view. In such case, artifacts (truncation errors) due to imperfect reconstruction result.

The system of this embodiment is intended to correct such truncation errors. First, the detectors D1, D2 and D3 are revolved around the human body under examination and incident gamma rays are counted in each step of revolution and at each location on the detecting surface to obtain SPECT data and TCT data at the same time. Next, the TCT data is subjected to truncation correction in accordance with a method to be described below. It should be noted here that the SPECT data and the TCT data need not necessarily be obtained at the same time and they may be obtained in sequence.

Figure 2:
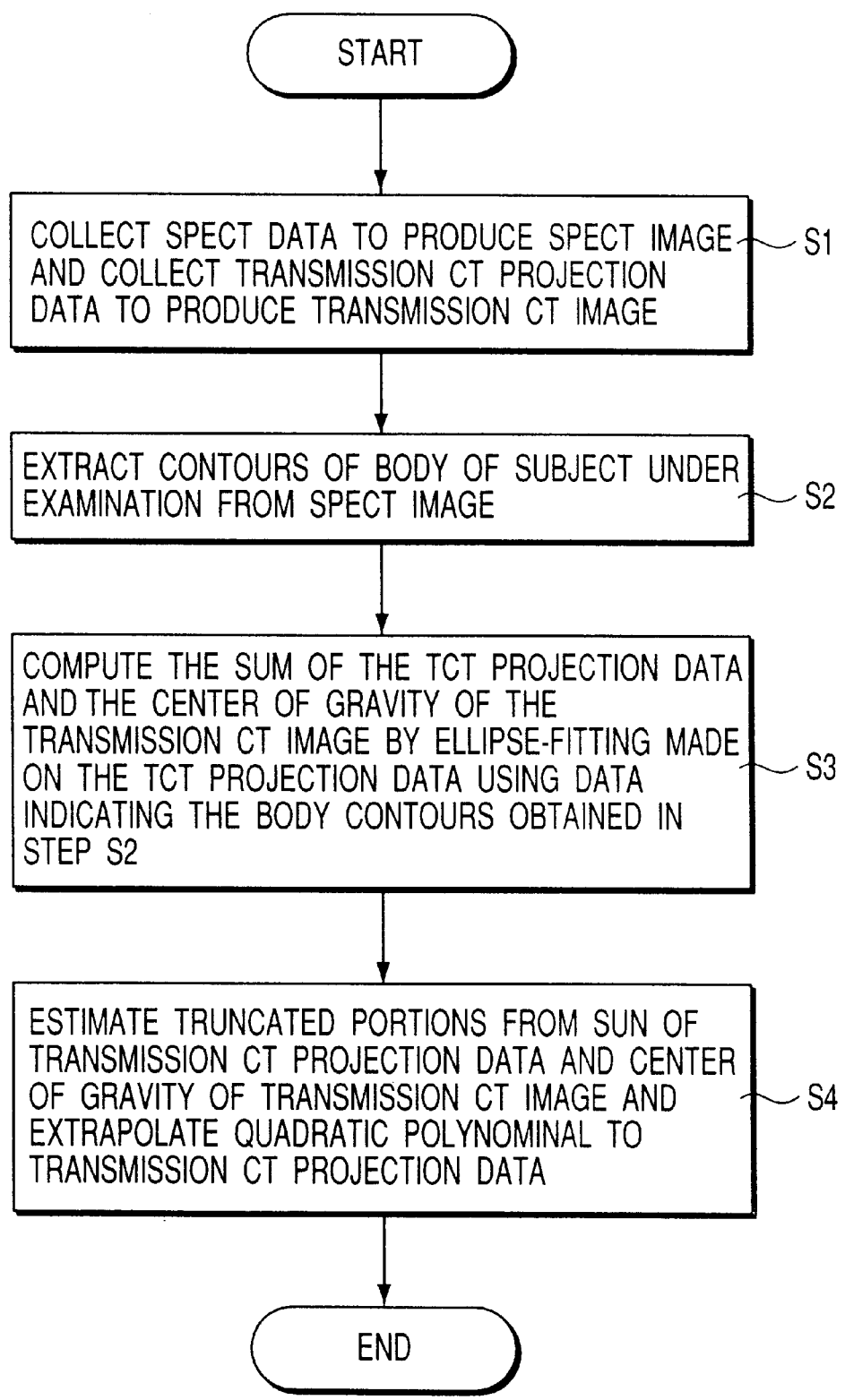
FIG. 2 is a flowchart for truncation correction of TCT data.

The basic principle of the truncation correction of this embodiment resides in employing the contours of the body of a subject under examination and the properties of TCT projection data. More specifically, the truncation correction is implemented by a sequence of operations consisting of steps S1 through S4 shown in FIG. 2.

In step S1, SPECT data is collected to obtain a SPECT image and transmission CT projection data is collected to obtain a transmission CT image. In step S2, the contours of the body of the subject under examination are extracted from the SPECT image. In step S3, a portion of the transmission CT projection data (between FOV and the body contours) is temporarily approximated by a curve (in this embodiment, for example, ellipse) using data indicating the body contours obtained in step S2 and then the sum of the curve-fitting transmission CT projection data and the center of gravity of the transmission CT image are computed. In step S4, the truncated portion is estimated on the basis of the sum of the transmission CT projection data and the center of gravity of the transmission CT image to correct the transmission CT projection data. The extraction of the contours of the body in step S2 is unnecessary if data of the same precision is obtained without the SPECT data.

For example, in this embodiment, the correction of the transmission CT projection data in step S4 is to produce anew a curve represented by a quadratic polynomial for the region (truncated region) for which ellipse-fitting has been made in order to determine the sum and the center of gravity. This procedure is referred to as extrapolation.

The radioactive medicine, such as RI, is frequently distributed throughout veins as well as object organs and hence it is possible to extract roughly the contours of a body from a SPECT image. The method of extracting the body contours in step S2 is to convert the SPECT data collected by the detector D1 through the truncation-free parallel hole collimator 10 into binary data by setting a threshold for each slice and backward-project the binary data.

It is desirable to smooth the determined contours by a Fourier fitting process of order of 7. Note that the order of Fourier fitting process is not limited to 7.

The truncation-free TCT data has a property that the sum of TCT projection data is constant in all the directions of projection and a property that the center of gravity of the TCT image, as viewed from all the directions of projection, is fixed.

In view of these properties, the following data processing is performed.

Figure 3:
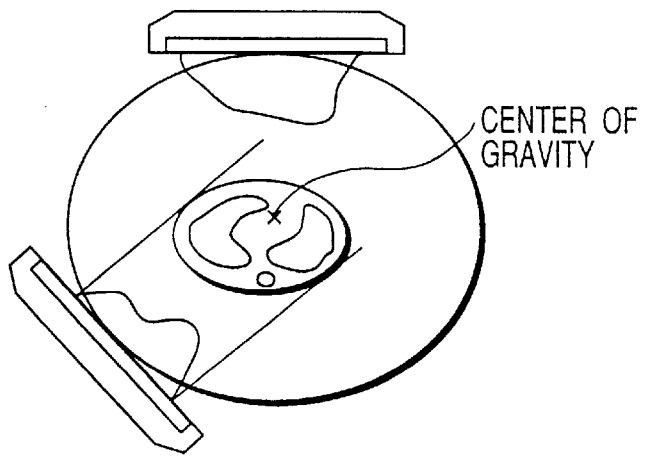
FIG. 3 shows TCT projection data and the center of gravity of a cross-sectional image of a human body under examination.
Figure 4A:
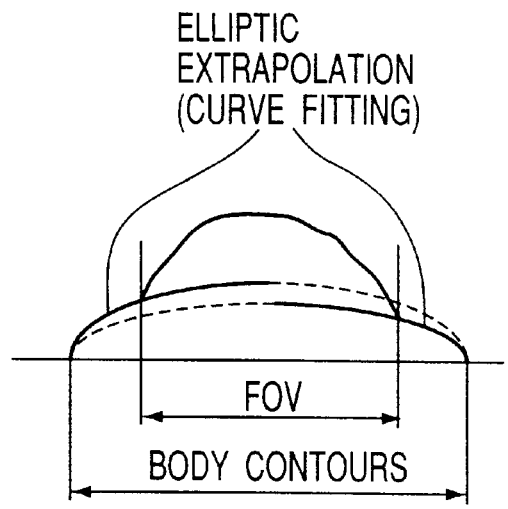
FIG. 4A shows extrapolation of an elliptic function to truncated portions.
Figure 4B:
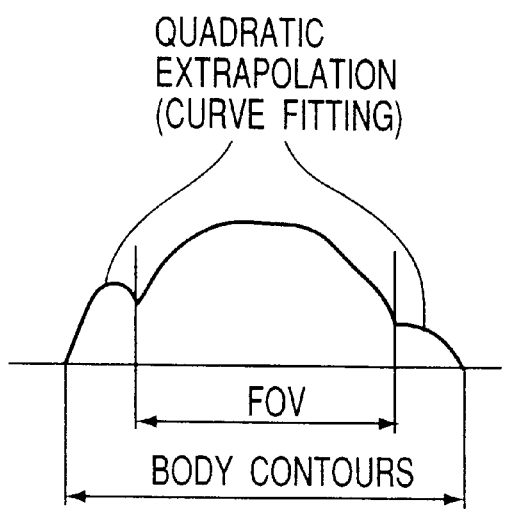
FIG. 4B shows extrapolation of a quadratic function to truncated portions.

FIG. 3 shows the TCT projection data and the center of gravity of the TCT image. FIG. 4 shows the manner of extrapolation to the truncated portions. More specifically, FIG. 4A shows extrapolation of an elliptic function and FIG. 4B shows extrapolation of a quadratic function.

First, in step S3, ellipse-fitting is made on the TCT projection data using data indicating the body contours obtained in step S2 and then the sum of the TCT projection data and the center of gravity of the transmission CT image are computed. Next, in step S4, the truncated portion is estimated from the sum of the TCT projection data and the center of gravity of the transmission CT image and then a quadratic is extrapolated to the transmission CT projection data.

In this manner, truncation correction can be made on the TCT projection data. The use of truncation-corrected TCT projection data allows the suppression of artifacts when a portion of the body of a subject under examination protrudes from the effective field of view of the collimator.

Thus, the distribution of coefficients of decay of gamma rays in the SPECT image can be measured with precision using such TCT data.

Here, the data processing in steps S3 and S4 will be described in detail.

Figure 5:
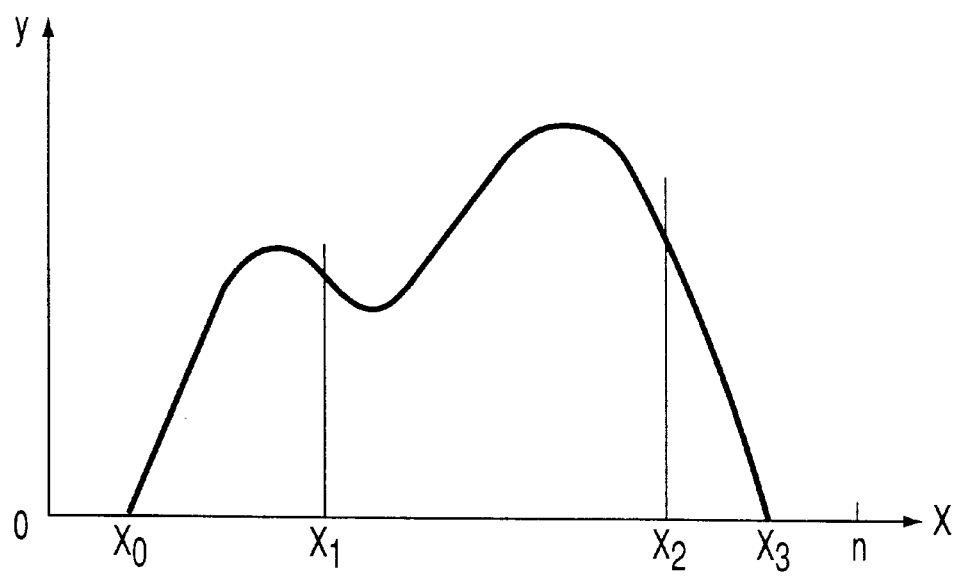
FIG. 5 shows a projection data profile.

FIG. 5 shows a profile of projection data. In this diagram, the count values of gamma rays are shown on the y axis and the position of projection data is shown on the x axis. n represents the matrix size of projection data and is set to be wider than the width of the body of the subject under examination. On the x axis, x0 to x3 represent the following positions:

x0: an edge of the body of the subject under examination determined from the body contour obtained from the SPECT data.

x1: an edge of the detector that collects the TCT data.

x2; the other edge of the detector that collects the TCT data.

x3; the other edge of the body of the subject under examination determined from the body contour obtained from the SPECT data.

And yd(x) represents the count of gamma rays actually detected by the detector between x1 and x2.

That is, the portion between x1 and x2 corresponds to the detecting surface of the detector and the portion between x0 and x3 corresponds to the width of the body of the subject under examination.

As described in step S3, the area (i.e., the sum) of transmission CT projection data for which an elliptic-function extrapolation approximation has been made is determined.

In the process of computation, assumptions are made such that (1) the function values at the edges of the body are 0 and (2) the function values and the measured values agree at the edges of the TCT projection data profile.

The elliptic-function extrapolation approximation will be described first. In FIG. 5, approximate values based on elliptic functions are inserted between x0 and x1 and between x2 and x3. In this case, an elliptic function such that the function values are 0 at x0 and x3 and yd(x1) at x1 is inserted between x0 and x1, and an elliptic function such that the function values are 0 at x0 and x3 and yd(x2) at x2 is inserted between x2 and x3.

Next, for transmission CT projection data having elliptic functions extrapolated, the sum (area) of counts of gamma rays over the projection data position range from 0 to n is determined based on the expression for the 0-th-order moment to be described later. Next, for transmission CT projection data having elliptic functions extrapolated, the center of gravity of counts of gamma rays over the projection data position range from 0 to n is determined based on the expression for the first-order moment to be described later. The work of determining the area and the center of gravity from the transmission CT projection data having elliptic functions extrapolated is carried out on projection data obtained in each angular step of revolution, with the result that the area and the center of gravity corresponding to each angular step of revolution are determined.

The area and the position of the center of gravity on the image determined in each angular step of revolution should become fixed according to the principles of the transmission CT. However, in practice they vary with the angle of rotation due to approximation errors. For this reason, one correct area and one correct position of the center of gravity are estimated from two or more areas and positions of center of gravity determined in angular steps of revolution. Specifically, the average of several measurements of the area selected in the order of magnitude beginning with the largest from all the measurements is taken to be the estimated value for the correct area. By determining a function that fits the positions of the center of gravity obtained in angular steps of revolution and corresponds to one point on two-dimensional coordinate system by the use of the least square method on a sinogram, the one point on the two-dimensional coordinate system is taken to be the estimated position of the center of gravity.

Next, the operation of step 4 will be described.

In step S4, low-degree polynomials (in particular, quadratic polynomials expected to keep relatively non-negativity) are used to estimate a curve y1 corresponding to the truncated portion between x0 and x1 and a curve y2 corresponding to the truncated portion between x2 and x3.

The curve y1 and the curve y2 are represented by y1(x)=$a_0$+$a_1$(x−$x_1$)+$a_2$(x−$x_1$)$^2$ ($X_0 \leq x < X_1$)

y2(x)=$a_4$+$a_5$(x−$x_2$)+$a_6$(x−$x_2$)$^2$ ($X_2 \leq x < X_3$)

The following conditions are set up on the curves y1 and y2 and the coefficients a0 to a6 that satisfy the conditions are found.

(1) When measured data yd(x) is extrapolated from the curves y1 and y2, the 0-th-order moment (area) of transmission CT projection data in each angular step of revolution agrees with the correct area estimated in step S3 and the first-order moment (center of gravity) of transmission CT projection data in each angular step of revolution agrees with the correct position of the center of gravity estimated in step S3.

(2) The values at the edges of the subject under examination found on the basis of the body contours determined from the SPECT data are predetermined ones. In this embodiment, y1(x0)=0 and y2(x3)=0

(3) The measured values at the edges of the detector that collects TCT data agree with values of curves y1 and y2 at the edges of that detector, respectively. That is, y1 (x1)=yd (x1) and y2(x2)=yd(x2)

The coefficients that satisfy the above conditions are as follows:

$$a_0 = y_1(x_1)$$

$$a_1 = \{12(M_1 - I_1) - 6(M_0 - I_0)(x_3 + x_2) +$$
$$a_4(x_3 - x_2)^2 + a_0(x_0 - x_1)(3x_0 + 5x_1 - 4x_2 - 4x_3)\}/$$
$$\{(x_0 - x_1)^2(-x_0 - x_1 + x_2 + x_3)\}$$

$$a_2 = (-a_0)/(x_0 - x_1)^2 - a_1(x_0 - x_1)$$

$$a_4 = y_2(x_2)$$

$$a_5 = \{12(M_1 - I_1) - 6(M_0 - I_0)(x_0 + x_1) -$$
$$a_0(x_0 - x_1)^2 - a_4(x_3 - x_2)(3x_3 + 5x_2 - 4x_1 - 4x_0)\}/$$
$$\{(x_3 - x_2)^2(-x_0 - x_1 + x_2 + x_3)\}$$

$$a_6 = (-a_4)/(x_3 - x_2)^2 - a_5/(x_3 - x_2)$$

The M0–I0 and M1–I1 are determined from the following 0-th-order moment and first-order moment:

[1] 0-th-order moment (area)

$$\begin{cases} \text{without truncation: } M_0 \\ \text{with trancation: } I_0 \end{cases}$$

$$M_0 - I_0 = \int_{x_0}^{x_1} y_1(x)\,dx + \int_{x_2}^{x_3} y_2(x)\,dx$$

[2] First-order moment (center of gravity)

$$\begin{cases} \text{without truncation: } M_0 \\ \text{with trancation: } I_0 \end{cases}$$

$$M_1 - I_1 = \int_{x_0}^{x_1} y_1(x) \cdot x\,dx + \int_{x_2}^{x_3} y_2(x) \cdot dx$$

The formulae for the 0-th and the first-order moment use M' obtained by considering the denominator in the general formula for the projection data shown in FIG. 5 to be fixed.

From the general formula for the 0-th-order moment $$M = \frac{\int_0^n y(x) \cdot dx}{\int_0^n dx}$$

we have $$M' = \int_0^n y(x) \cdot dx$$

From the general formula for the first-order moment $$M = \frac{\int_0^n y(x) \cdot x\,dx}{\int_0^n x\,dx}$$

we have $$M' = \int_0^n y(x) \cdot x\,dx$$

The curves y1 and y2 determined in the above manner are extrapolated to both sides of the actually measured data yd(x), thereby obtaining transmission CT projection data corrected by quadratic extrapolation. This work is carried out on transmission CT projection data obtained at each angular step of revolution, thereby obtaining quadratic extrapolation-corrected transmission CT projection data at each step of revolution.

By using the quadratic extrapolation-corrected transmission CT projection data thus obtained, a cross-sectional image of the human body under examination can be reconstructed to obtain a good transmission CT image.

The following specific advantages of the above-described embodiment were confirmed.

Using cardiac muscle SPECT clinical data collected by TCT having a fan beam collimator with a focal length of 80 cm, pseudo-TCT data involving truncation was prepared by narrowing down the effective field of view and truncation correction was made on that data. The clinical data were obtained from a big American woman and an average Japanese man. The system's minimum field of view was assumed to be 220 mm in diameter.

This embodiment confirmed that truncation correction could be made with precision even on TCT data obtained from an uneven body region such as a woman's bust. The evaluation of SPECT data having decay of gamma rays compensated for using TCT data subjected to such truncation correction verified that SPECT data artifacts resulting from truncation were suppressed.

More specifically, the evaluation of SPECT values in a sectional image along a short axis verified that an error of 20% before correction was reduced below 6% after correction.

Although the preferred embodiment of the present invention has been disclosed and described, it is apparent that other embodiments and modifications are possible.

According to the present invention, as described above, a practical apparatus and method can be provided which allow precise TCT data having truncation errors corrected to be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. truncation correction apparatus for transmission CT comprising:
   first acquiring means for acquiring emission data;
   second acquiring means for acquiring TCT projection data;
   calculating means for calculating a center of gravity of a TCT image and a total of the TCT projection data from the emission data and the TCT projection data; and
   correcting means for correcting the TCT projection data on the basis of the center of gravity of the TCT image and the total of the TCT projection data.

2. The apparatus according to claim 1, wherein said correcting means includes:
   estimating means for estimating a truncated portion of the TCT projection data on the basis of the center of gravity of the TCT image and the total of the TCT projection data; and
   means for correcting the TCT projection data on the basis of an estimation result of the estimating means.

3. The apparatus according to claim 1, wherein said calculating means includes:
   a first calculating section for calculating tentative data of a truncated portion of the TCT projection data from the emission data and the TCT projection data;
   first TCT projection data generating means for generating first TCT projection data by replacing the truncated portion of the TCT projection data with the tentative data; and
   means for calculating the center of gravity of the TCT image and a total of the first TCT projection data on the basis of the first TCT projection data;
   and said correcting means includes:
   a second calculating section for calculating final data of the truncated portion of the TCT projection data from the total of the first TCT projection data and the gravity of center of the TCT image; and
   means for replacing the truncated portion of the TCT projection data with the final data.

4. The apparatus according to claim 3, wherein a curve indicative of the final data is more precise than a curve indicative of the tentative data.

5. The apparatus according to claim 4, wherein the curve indicative of the tentative data includes an elliptic curve.

6. The apparatus according to claim 4, wherein the curve indicative of the final data includes a curve at least represented by a quadratic polynomial.

7. The apparatus according to claim 1, wherein said emission data is SPECT data without truncation.

8. A truncation correction apparatus for transmission CT comprising:
   first acquiring means for acquiring data indicative of a body contour of a subject to be examined;
   second acquiring means for acquiring TCT projection data;
   calculating means for calculating a center of gravity of a TCT image and a total of the TCT projection data from data indicative of the body contour and the TCT projection data; and
   correcting means for correcting the TCT projection data on the basis of the center of gravity of the TCT image and the total of the TCT projection data.

9. The apparatus according to claim 8, wherein said correcting means includes:
   estimating means for estimating a truncated portion of the TCT projection data on the basis of the center of gravity of the TCT image and the total of the TCT projection data; and
   means for correcting the TCT projection data on the basis of an estimation result of the estimating means.

10. The apparatus according to claim 8, wherein said calculating means includes:
    a first calculating section for calculating tentative data of a truncated portion of the TCT projection data from the data indicative of the body contour and the TCT projection data;
    first TCT projection data generating means for generating first TCT projection data by replacing the truncated portion of the TCT projection data with the tentative data; and
    means for calculating the center of gravity of the TCT image and a total of the first TCT projection data on the basis of the first TCT projection data;
    and said correcting means includes:
    a second calculating section for calculating final data of the truncated portion of the TCT projection data from the total of the first TCT projection data and the gravity of center of the TCT image; and means for replacing the truncated portion of the TCT projection data with the final data.

11. The apparatus according to claim 10, wherein a curve indicative of the final data is more precise than a curve indicative of the tentative data.

12. The apparatus according to claim 11, wherein the curve indicative of the tentative data includes an elliptic curve that at least passes the body contour and an edge of the TCT projection data.

13. The apparatus according to claim 11, wherein the curve indicative of the final data includes a curve that at least passes the body contour and an edge of the TCT projection data and is at least represented by a quadratic polynomial.

14. A correction apparatus for transmission CT comprising:
   first collection means for collecting SPECT data to produce a SPECT image;
   second collection means for collecting transmission CT projection data to produce a transmission CT image;
   extract means for extracting the contours of the body of a subject under examination from the SPECT image collected by the first collection means;
   computing means for computing the sum of the transmission CT projection data and the center of gravity of the transmission CT image after curve-fitting using the data representing the contours of the body has been made; and
   truncation correcting means for estimating a truncated portion on the basis of the sum of the transmission CT projection data and the center of gravity of the transmission CT image and correcting the transmission CT projection data.

15. The apparatus according to claim 14, wherein the curve fitting includes elliptic fitting.

16. The apparatus according to claim 14, wherein the truncation correction means adds a curve represented by a quadratic polynomial to the estimated truncated portion of the transmission CT projection data.

17. The apparatus according to claim 14, wherein the second collection means includes a surface source of nuclear species different from that of the first collection means, a fan beam collimator placed to be opposed to the surface source with the subject under examination interposed therebetween, and means for varying the position of the fan beam collimator relative to the surface source.

18. The apparatus according to claim 14, further comprising conversion means for converting fan beam-based transmission CT projection data obtained by the second collection means into parallel beam data.

19. The apparatus according to claim 14, further comprising smoothing means including seventh-order Fourier fitting processing for smoothing the contours of the body extracted by the extract means.

20. A nuclear medical diagnostic apparatus comprising:
   first collection means for collecting SPECT data to produce a SPECT image;
   second collection means for collecting transmission CT projection data to produce a transmission CT image;
   extract means for extracting the contours of the body of a subject under examination from the SPECT image collected by the first collection means;
   computing means for computing the sum of the transmission CT projection data and the center of gravity of the transmission CT image by curve-fitting using data representing the contours of the body;
   truncation correcting means for estimating a truncated portion on the basis of the sum of the transmission CT projection data and the center of gravity of the transmission CT image and correcting the transmission CT projection data; and
   decay correcting means for subjecting the SPECT image to decay correction on the basis of the TCT projection data having its truncated portion corrected.

21. The apparatus according to claim 20, wherein the collection of the SPECT data by the first collection means and the collection of the transmission CT projection data by the second collection means are made at the same time.

22. A method for correcting truncation of transmission CT projection data on the basis of SPECT data and the transmission CT projection data comprising the steps of:
   extracting the contours of the body of a subject under examination from the SPECT image;
   computing the sum of the transmission CT projection data and the center of gravity of a transmission CT image by curve fitting using data representing the contours of the body; and
   estimating a truncated portion on the basis of the sum of the transmission CT projection data and the center of gravity of the transmission CT image and correcting the transmission CT projection data.

23. A method for correcting truncation of transmission CT projection data on the basis of SPECT data and the transmission CT projection data comprising the steps of:
   extracting the contours of the body of a subject under examination from the SPECT image;
   computing the estimated sum of the transmission CT projection data and the estimated center of gravity of a transmission CT image on the basis of the transmission CT projection data and data representing the contours of the body; and
   correcting the truncation of the transmission CT projection data so that the sum of the transmission CT projection data obtained at each angular step of revolution and the position of the center of gravity of the transmission CT image agree with the estimated sum and the estimated position of the center of gravity, respectively.

* * * * *